United States Patent [19]

Money et al.

[11] Patent Number: 4,466,440
[45] Date of Patent: Aug. 21, 1984

[54] HEART PACER TIME-DOMAIN PROCESSING OF INTERNAL PHYSIOLOGICAL SIGNALS

[75] Inventors: David K. Money, Pennant Hills; Andrew D. MacLaurin, North Epping, both of Australia

[73] Assignee: Telectronics Pty. Ltd., Lane Cove, Australia

[21] Appl. No.: 320,338

[22] Filed: Nov. 12, 1981

[51] Int. Cl.³ .............................................. A61N 1/36
[52] U.S. Cl. ............................. 128/419 PG; 128/696
[58] Field of Search ............... 325/38 B; 128/419 PG, 128/696, 702, 704, 706, 708, 710, 711; 3/1.7

[56] References Cited

U.S. PATENT DOCUMENTS

| | | | |
|---|---|---|---|
| 3,418,662 | 12/1968 | Bottomley et al. | 3/1.1 |
| 3,557,796 | 1/1971 | Keller, Jr. et al. | 128/419 PG |
| 3,868,567 | 2/1975 | Ekstrom | 128/704 |
| 3,902,479 | 9/1975 | Chaumet | 128/703 |
| 4,388,927 | 6/1983 | Schober | 128/419 PG |

*Primary Examiner*—William E. Kamm
*Attorney, Agent, or Firm*—Gottlieb, Rackman & Reisman

[57] ABSTRACT

There is disclosed a heart pacer in which the sensed signal is processed in the time domain rather than the frequency domain. A delta modulator operates directly on the sensed electrogram signal, without any intervening filtering, to derive a sequence of bits whose states represent increments or decrements in the sensed signal amplitude. Decisions as to cardiac activity are based on the sequence of bit values thus generated. The particular delta modulator disclosed is highly advantageous in that it allows highly accurate tracking and representation of the sensed signal.

23 Claims, 14 Drawing Figures

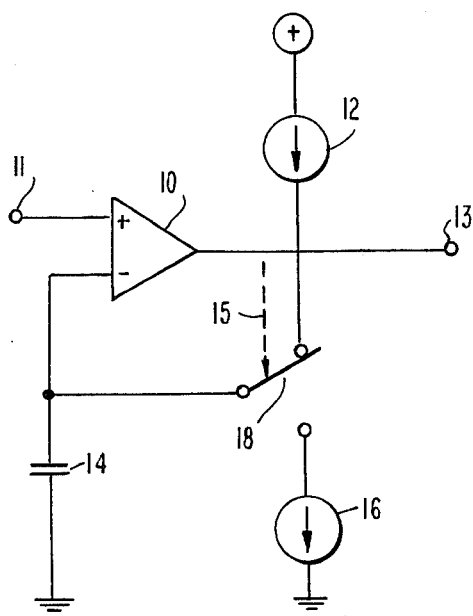
FIG. 1
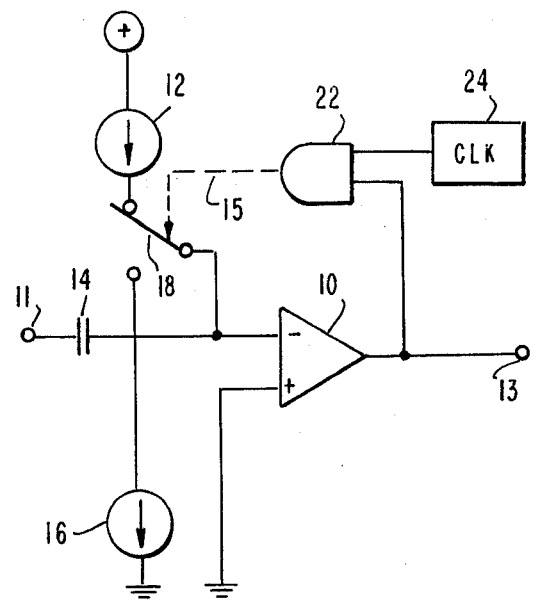
FIG. 2
FIG. 3A
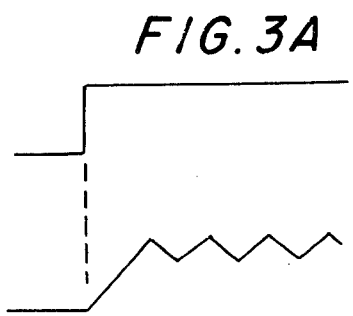
FIG. 3B
FIG. 4A
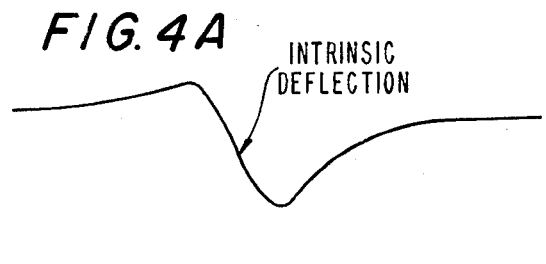
FIG. 4B
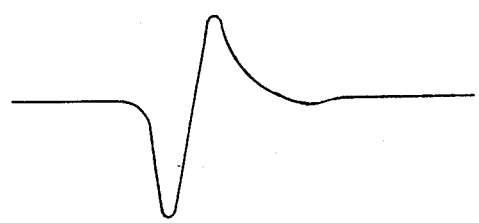
FIG. 4C

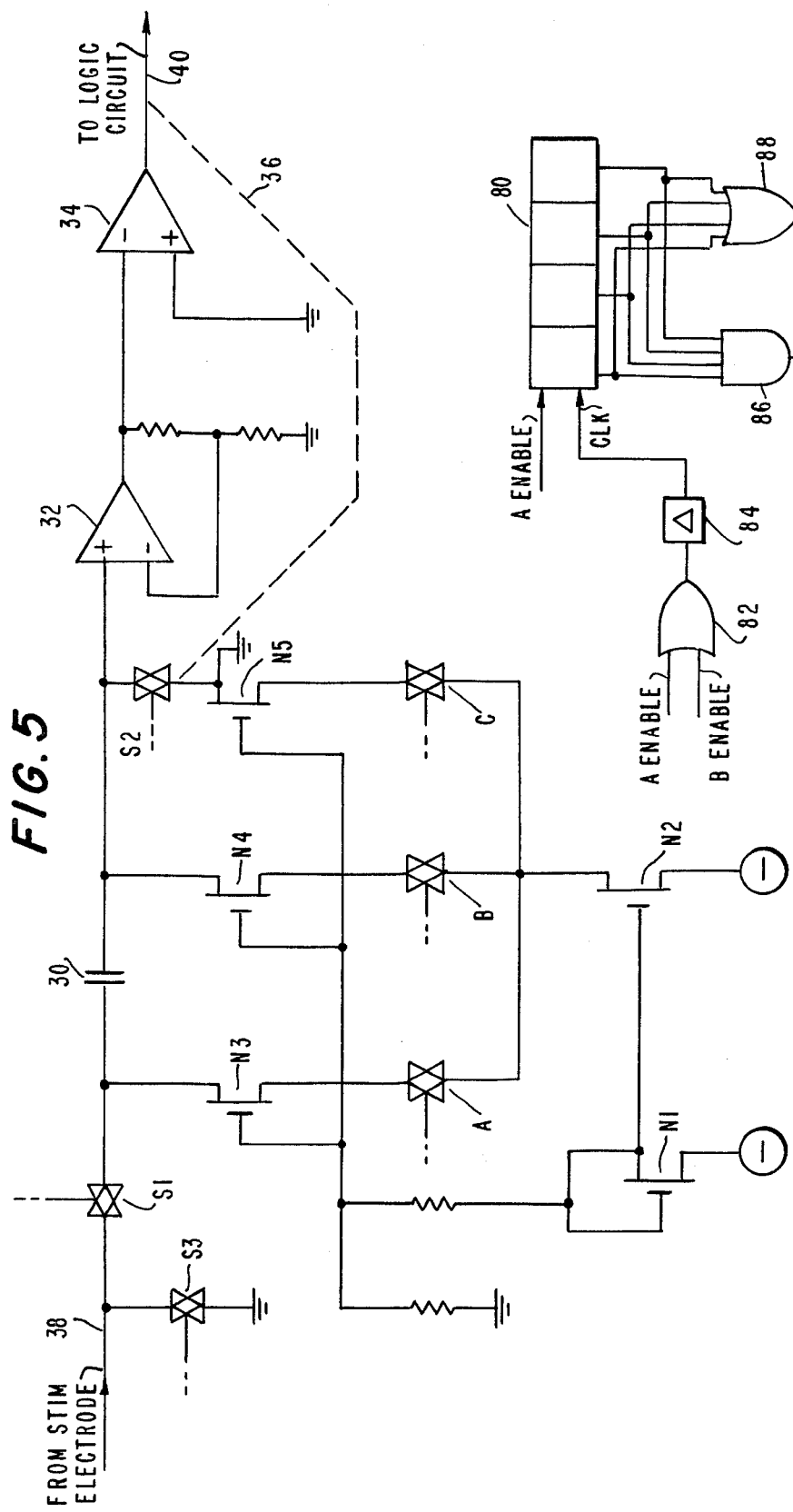

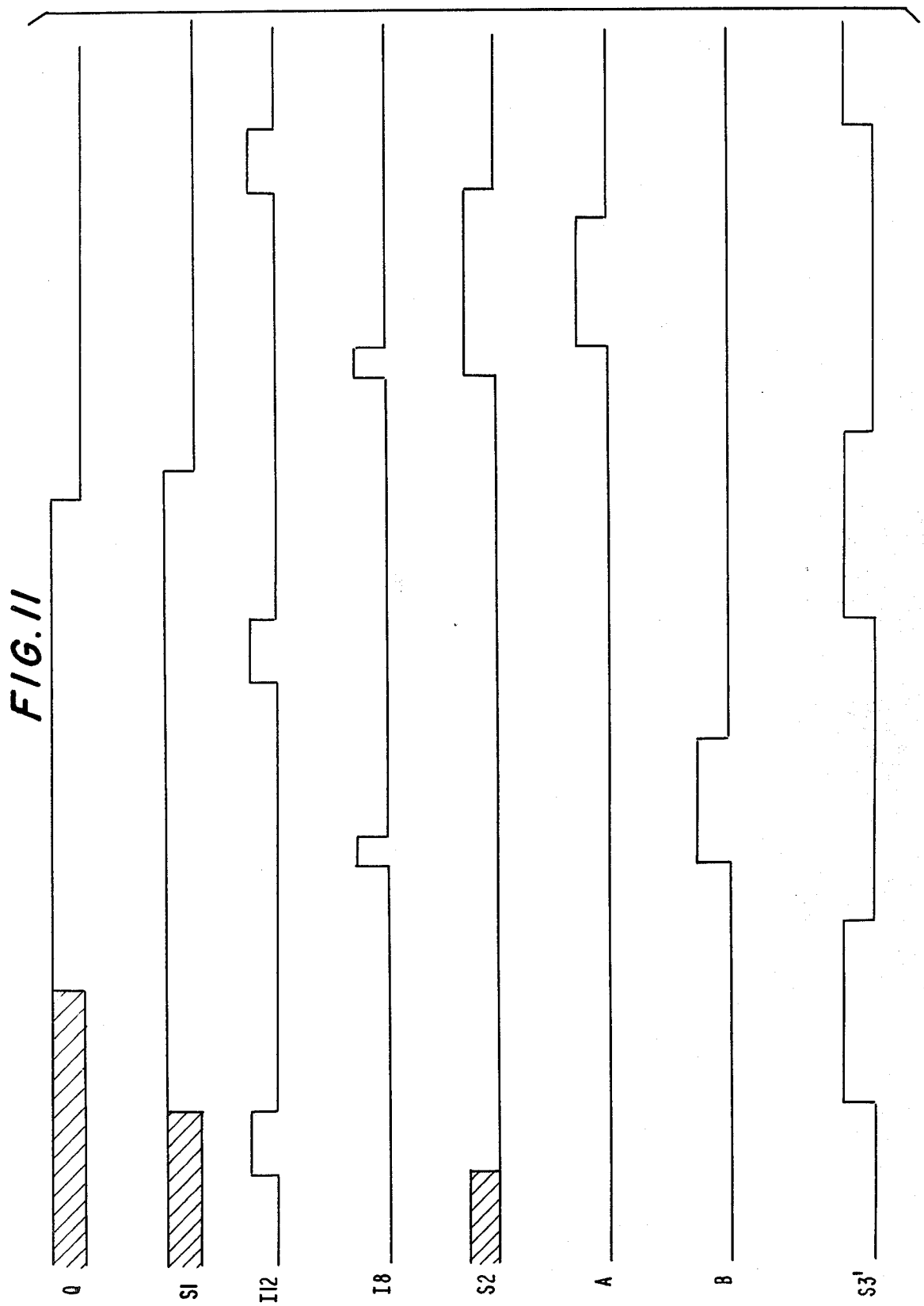

HEART PACER TIME-DOMAIN PROCESSING OF INTERNAL PHYSIOLOGICAL SIGNALS

DESCRIPTION

This invention relates to time-domain processing of internal physiological signals by an implantable medical prosthesis, and more particularly to the digital processing of electrical heart activity signals for controlling the operation of an implantable heart pacer.

A typical heart pacer is controlled by sensing electrical activity in the heart and appropriately generating stimulating current pulses. The sensed signal is, of course, in analog form. Although many of the timing functions performed by a present-day pacer are digitally controlled, the input signal processing is analog in nature. The input section of the pacer invariably includes discrete components which filter the sensed signal; for example, traditional R-wave sensing usually entails the use of a filter with a 20–100 Hz bandpass centered at 50 Hz. The analog frequency-domain processing usually leads to the recognition of a single discrete event, e.g., a ventricular contraction, following which digital processing may ensue.

However, it would be highly advantageous to utilize digital processing even in the input stage of a pacer and, in fact, implantable monitoring devices of all kinds. The use of digital, rather than analog, processing would not only reduce the number of bulky discrete components which must be included in the implantable device, but it would also minimize the number of adjustments which must usually be made during manufacture as well as variations from unit to unit. Converting the sensed signal from analog to digital form, without preliminary analog processing, offers the possibility of total signal processing in the time domain. Furthermore, by operating in the digital realm even in the early stages of processing, it should be possible to transmit to an external monitor a more accurate representation of the sensed signal (even if the implanted device serves solely in a monitoring/telemetring capacity without even providing any form of electrical stimulation).

It is a general object of our invention to provide total time-domain processing of an internal physiological signal by converting the sensed signal to digital form at the input of the system which operates upon the signal.

It is another object of our invention, in the preferred embodiment thereof, to thus convert the sensed signal without requiring the use of a conventional multi-bit analog-to-digital converter in order that the input stage of the implantable device be of minimal size and complexity.

There is a coding technique known as delta modulation which has long been used in communications systems. It is of course standard to convert an analog signal into digital samples which, after transmission, are used to reconstruct the original signal. For example, each analog signal sample might be converted into an 8-bit digital code, the 8-bit sample then being transmitted either in parallel or serial form. In accordance with well-known principles of information theory, as long as the samples are taken at a high enough rate, the reconstructed analog signal will accurately represent the original. Delta modulation involves not the transmission of the magnitude of each sample, but rather the difference between the magnitude of the current sample and the magnitude of the previous sample. Especially in the case of slowly-changing signals, it requires fewer bits to represent sample differences than it does to represent the samples themselves.

The simplest form of delta modulation involves the transmission of single-bit sample differences. The transmission of a 0 simply means that the current sample is smaller in magnitude than the magnitude of the previous sample; a bit of value 1 represents an increase in sample magnitude. A large increase in the analog signal of interest may result in a long succession of bits of value 1. At the receiving end of the transmission link, the reconstructed signal increases in a step-wise fashion for each received bit of value 1. Similar remarks apply to the transmission of a sequence of 0's as the analog signal to be processed decreases in amplitude. A steady-state analog signal simply results in the transmission of alternate 0's and 1's.

A delta modulation coding scheme of the type described has been proposed for the telephonic transmission of electrocardiographic signals. (See, e.g., Suthasinekul, "Adaptive Delta Modulation For Telephone Bioelemetry Of ECG", June, 1979, National Technical Information Service Publication No. PB80-160773.) But while delta modulation has been proposed for communication purposes, and even for the recording of information, it has not been recognized that the technique can be used for the entirely different purpose of converting an internal physiological signal into the time domain, and then processing the resulting bit stream without requiring any analog processing. In accordance with the principles of our invention, we convert an internal physiological signal into digital form directly, without first providing for analog processing. Whether or not the digital form of the signal is actually transmitted externally, it is as a result of the initial conversion that the bulk, variability and complexity of an implanted device may be minimized.

Although other analog-to-digital conversion schemes may be utilized, the use of single-bit delta modulation is highly preferred in that it allows the relatively simple conversion of an analog signal at an electrode to a bit stream. Especially in the case of systems for monitoring the electrical signals which represent heart activity, delta modulation is preferred because the analog signal to be processed is relatively slow-changing, and single-bit difference samples at moderate rates in the kiloHertz range suffice.

Further objects, features and advantages of our invention will become apparent upon consideration of the following detailed description in conjunction with the drawing, in which:

FIGS. 1 and 2 depict two circuits which illustrate the general manner in which an analog signal can be converted to a bit stream by the use of delta modulation;

FIGS. 3A and 3B depict the manner in which the bit stream derived by either of the circuits of FIGS. 1 and 2 can be used to reconstruct an input analog signal;

FIG. 4A depicts a typical analog signal which is processed by the illustrative heart pacer of our invention, with FIGS. 4B and 4C representing the first and second derivatives of this signal;

Figure 6:
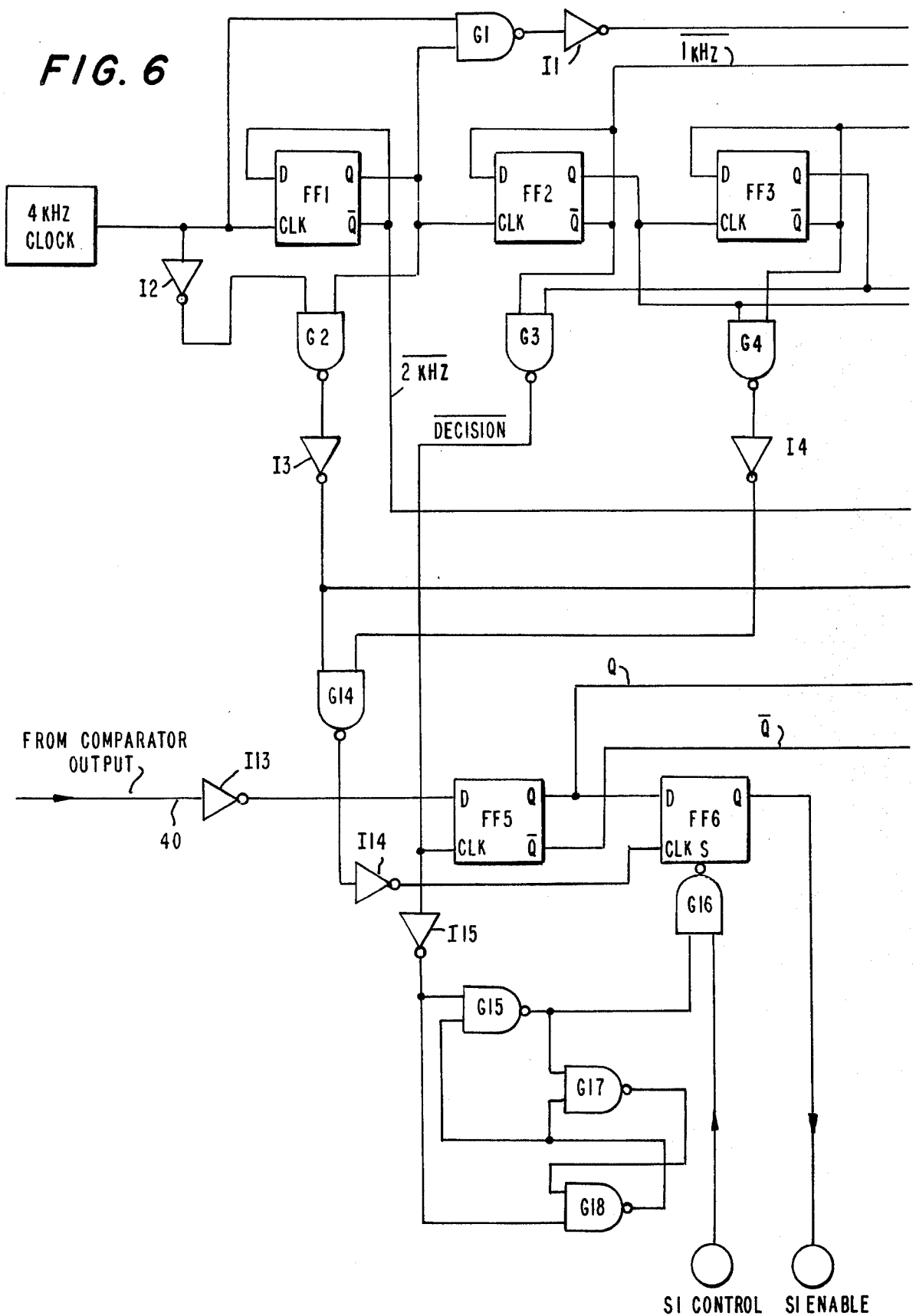
Figure 7:
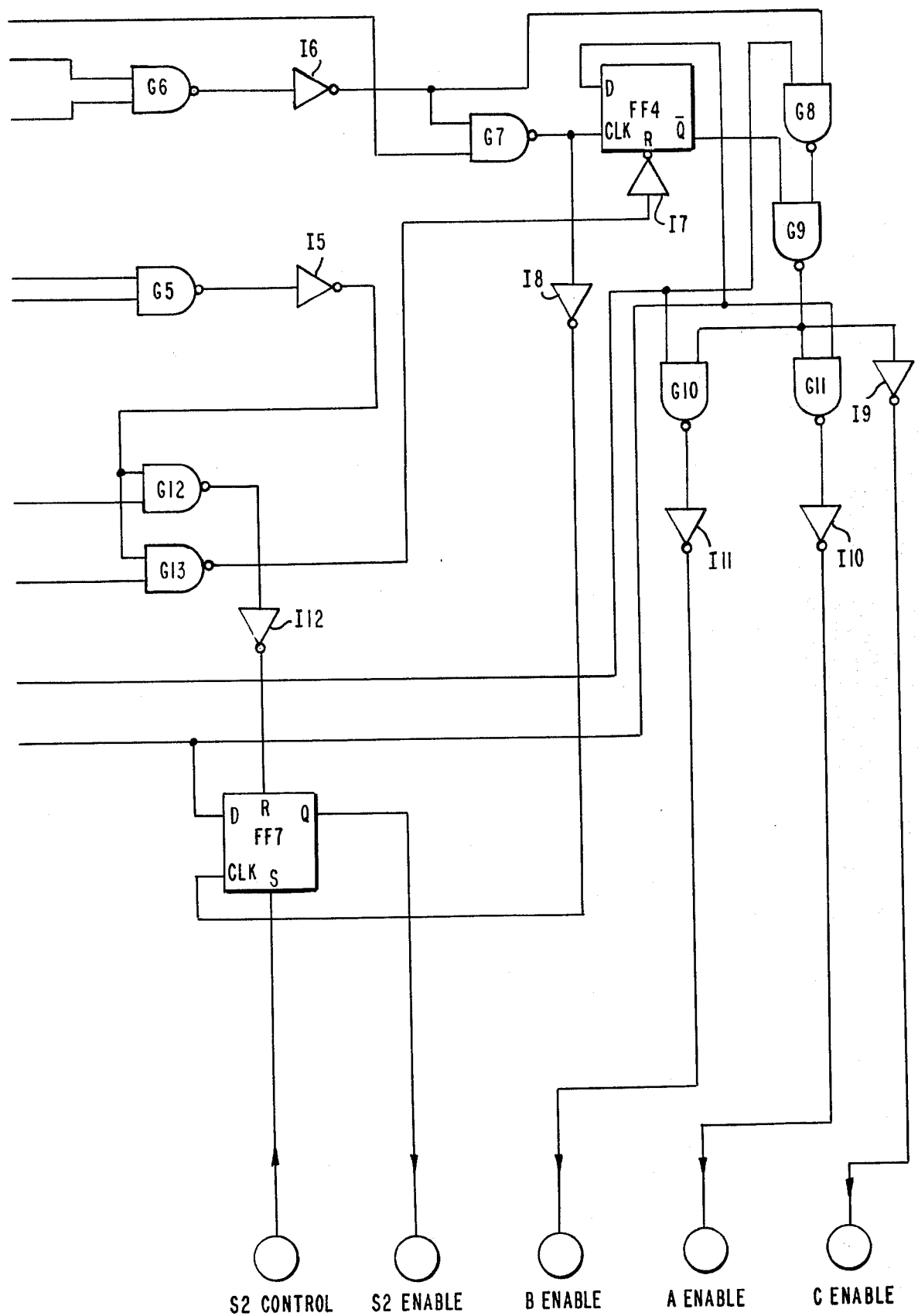
Figure 10:
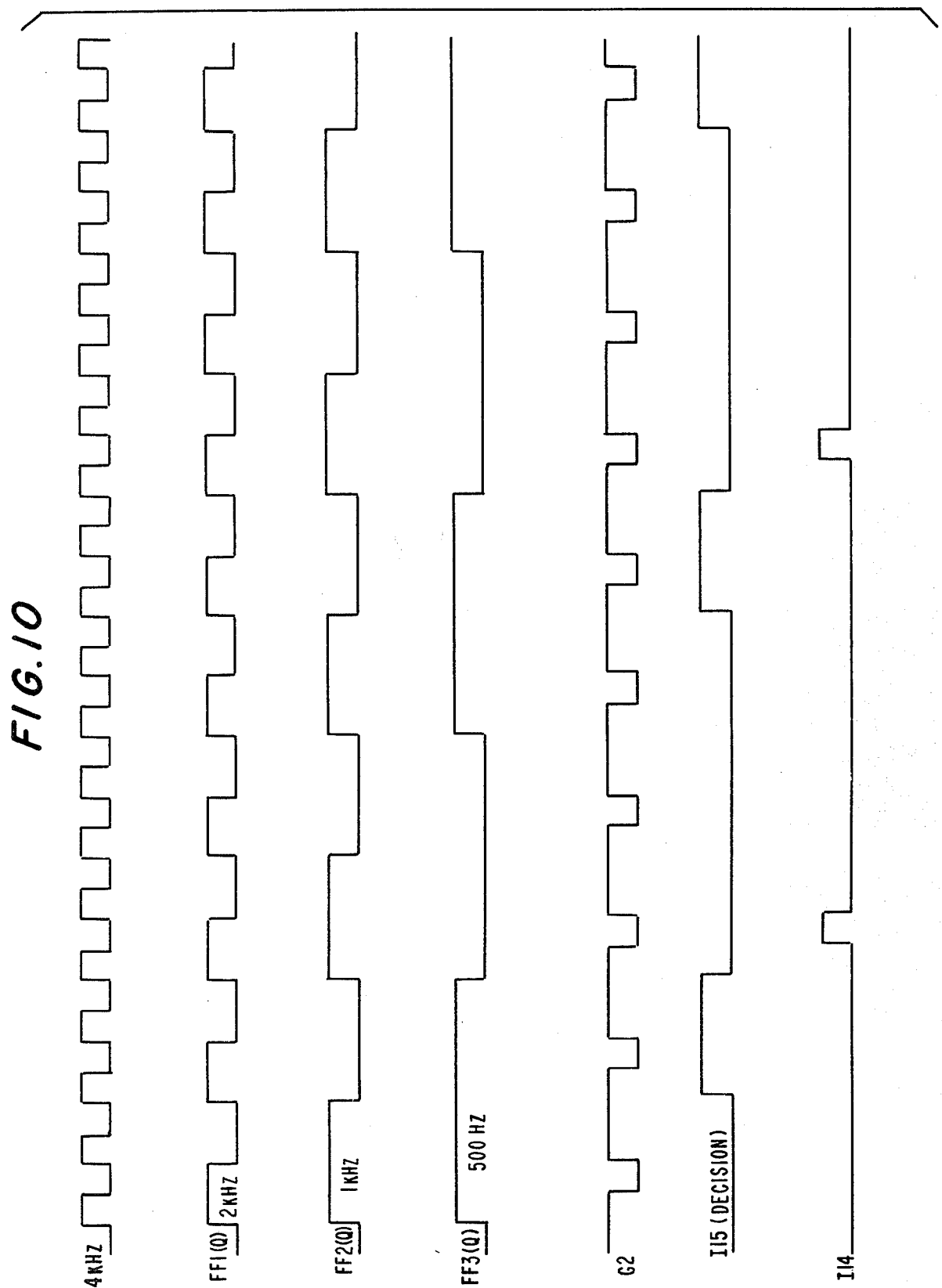

FIGS. 5–9 together represent the illustrative embodiment of our invention, with FIG. 6 of the logic circuit being placed to the left of FIG. 7; and FIGS. 10 and 11, with FIG. 10 being placed on top of FIG. 11, depict certain timing waveforms which will facilitate an understanding of the operation of the logic circuit of FIGS. 6 and 7.

The circuit of FIG. 1 is a simple delta modulator for converting an analog signal at input terminal 11 into a digital bit stream at output terminal 13. The input signal is applied to the plus input of comparator 10. The output of the comparator is high or low, representing a square wave at output 13. (The simple circuit of FIG. 1, which is not preferred in the first place, does not include a mechanism for changing the output only at discrete clock intervals.) The dashed line 15 symbolizes the control over switch 18 by the output of the comparator. When the comparator output is high, the switch is in the position shown; when the output is low, the switch is in its other position.

Capacitor 14 functions as an integrator. Suppose that the potential of the input signal at terminal 11 is greater than the potential across the capacitor. Since the capacitor potential appears at the minus input of the comparator, the output of the comparator will be high. In such a case, current source 12 is connected through switch 18 to charge capacitor 14. The output of the comparator remains high and the switch remains in the position shown until the voltage across capacitor 14 exceeds that at the input terminal. When the output of the comparator now goes low, switch 18 changes position and current source 16 serves to discharge the capacitor. The overall effect is that the comparator output controls the position of switch 18 so that the voltage of capacitor 14 tracks the voltage at the input terminal. The potential at terminal 13 indicates whether the input signal is increasing or decreasing. By using the square wave signal at terminal 13 to control the charging and discharging of another capacitor, e.g., after transmission to another site, the voltage across that other capacitor can be made to track the voltage at terminal 11. Of course, since constant current sources 12 and 16 cannot instantaneously charge and discharge capacitor 14, any signal reconstructed from the waveform at terminal 13 would be be slew-rate limited.

Quite apart from the fact that the system of FIG. 1 is not clocked so that its output is not truly a bit stream, the circuit cannot handle input signal variations over a wide range. The circuit of FIG. 2 not only provides a clocked bit stream, but it also handles a wider range of input signals. Capacitor 14 is now charged or discharged directly through the source impedance which appears at terminal 11. The plus input of comparator 10 is now grounded. Suppose, for example, that the input signal increases and a positive potential appears at the minus input of the comparator. The output of the comparator is thus low and, ignoring the effect of gate 22 and clock 24, the low potential causes switch 18 to change position. Current source 16 thus allows the capacitor to charge, lowering the potential at the minus input of the comparator. On the other hand, if the potential at the minus input of the comparator is negative, the output is high, switch 18 remains in the position shown, and current source 12 causes an oppositely directed current to flow, returning the potential at the minus input of the comparator to ground. Larger signal swings at the minus input of the comparator can be handled; the input signal voltage swing is limited only by the voltage rating of capacitor 14, and the input signal limiting-slew rate is limited only by the value of capacitor 14 and the average value of the charging current.

Clock 24 periodically enables gate 22. It is only when the gate is first enabled that switch 18 can change position. Dashed line 15 is symbolic only; an actual implementation of the circuit depicted in FIG. 2 might include a latch mechanism which would be set or reset with the generation of each clock pulse. Once the switch assumes a position, it remains there until the next clock pulse arrives. Thus the output of comparator 10 affects the switch position only once during each clock cycle. It should be noted that the potential at terminal 13 may actually change in the middle of a clock cycle as capacitor 14 continues to charge or discharge. It is the state of switch 18, and the state of the latch which controls it, which are more truly representative of the serial bit values because they change only at fixed intervals. Similarly, a latch between the output of the comparator and terminal 13 would serve the same purpose, with the latch being allowed to change only upon the generation of a clock pulse.

Assuming that the incremental change in capacitor potential, whether an increase or a decrease, is the same during each clock cycle, it is apparent that the magnitude of a step change in the input signal is reflected by the number of successive 0 or 1 bits which are generated in succession. Only after the capacitor potential matches that of the input signal are 0 and 1 bits alternately generated.

FIG. 3A depicts an analog signal in the form of a step, and FIG. 3B depicts the manner in which the same signal might be reconstructed by the bit stream derived by a delta modulator. Each bit of value 1, representing the charging of capacitor 14, would result in a discrete increment in the reconstructed signal. The increments occur only at the rate at which samples are taken in the first place. The dashed line in FIG. 3B, which follows the rise in the reconstructed signal, is designed to show that the overall system is slew-rate limited. The reconstructed signal cannot follow rapid changes in the signal to the processed, just as the potential across capacitor 14 cannot be adjusted instantaneously; it takes a finite time until enough bits of value 1 are received before the reconstructed signal reaches a level equal to that of the input signal which is being processed. The dashed line in FIG. 3B represents the fastest rate at which the reconstructed signal can change. It will also be noted in FIG. 3B that once a "steady state" condition is reached, the reconstructed signal actually alternately changes by single increments in the two opposite directions. This is because switch 18 always controls either the charging or discharging of capacitor 14, and consequently the resolution of the system is limited by the magnitude of each increment taken in the reconstructed signal upon the arrival of a 1 or 0 bit.

While the slew-rate and resolution considerations apply to all delta modulator circuits, and in fact to all digital sampling schemes, the waveforms of FIGS. 3A and 3B highlight a fundamental problem with the circuit of FIG. 2. For proper operation, current sources 12 and 16 should have the identical magnitude. If they do not, slow changes in the input signal being monitored may not even be recognizable.

This can be understood by considering a hypothetical example in which one of the two current sources is larger in magnitude than the other by 10%. For a constant input signal, this means that switch 18 will have to be in one position eleven times corresponding to its being in the other position only ten times; this is the only way in which the net average charge delivered to capacitor 14 can be zero when the two current sources differ in magnitude by 10%. The resulting bit stream will contain eleven bits of one value for each ten bits of the other, and there is no way to tell whether this is due to the inherent error of the system or to an input which is really changing. Thus the percentage difference between the two current-source magnitudes prevents recognition of changes in the input signal which occur at a rate lower than 10% of the slew rate. As will become apparent below, in the preferred embodiment of our invention a mechanism is provided for ensuring that the integrating capacitor is charged or discharged by currents whose magnitudes are virtually identical.

Before proceeding to a description of the illustrative embodiment of our invention, however, it will be helpful to understand the kind of physiological signal which is to be processed. The conventional electrocardiographic signal represents a skin surface potential. The signal is really a time and space integral in that it is affected by electrical activity over a wide body region, and there are unequal delays in signal arrival from each part of the region to the element of skin at which the monitoring takes place. On the other hand, FIG. 4A depicts what is known as an "electrogram" signal, the type of signal which appears at an electrode connected to the heart tissue itself. Ventricular contraction results in a conspicuous signal segment known as the "intrinsic deflection", whose duration is approximately 10 milliseconds. It is the intrinsic deflection segment of the overall electrogram which is the best indication of ventricular contraction, the phenomenon of concern in a typical pacer utilized to stimulate ventricular contractions.

However, rather than to process the electrogram signal itself, it is possible to process a signal representing its first derivative (FIG. 4B) or a signal representing its second derivative (FIG. 4C). It is in fact the second derivative which allows the most accurate measurement to be made of the duration of the intrinsic deflection. Although in the illustrative embodiment of the invention it is the encoded electrogram signal itself which is processed directly, it should be understood that in some cases it may be desirable to process the first derivative or second derivative of the signal. The derivative signals may actually be formed digitally without requiring the use of differentiators with discrete components. In other words, a bit stream representing constant-step increases and decreases in the electrogram signal may be converted into digital values representing samples of the derivative signals. In such a case, there is still no initial processing in the frequency domain, and the immediate conversion of the input signal to a bit stream allows all of the processing to be performed in the time domain.

It should also be understood that in many cases it will not even be necesary to utilize a discrete capacitor connected to the electrode at which the electrogram signal appears, such as capacitor 14 in FIGS. 1 and 2. Body fluids are electrolytic in nature, and result in a natural capacitive effect which may allow the input coupling capacitor to be dispensed with. In the system of FIGS. 5–9, however, a separate capacitor 30 (see FIG. 5) is charged and discharged in a manner comparable to that of capacitor 14 in FIG. 2.

FIG. 5 depicts the basic delta modulator of our invention. Lead 38 is connected to the stimulating electrode, and a bit stream appears on output conductor 40. Element 32 is a high-gain operational amplifier whose output is coupled to the minus input of comparator 34. Together, the two elements comprise a high-sensitivity comparator. An important feature of the circuit of FIG. 5 is that the same current derived from transistor N2 is made to flow through capacitor 30 in the two different directions, depending upon whether capacitor 30 is to be charged or discharged.

Figure 8:
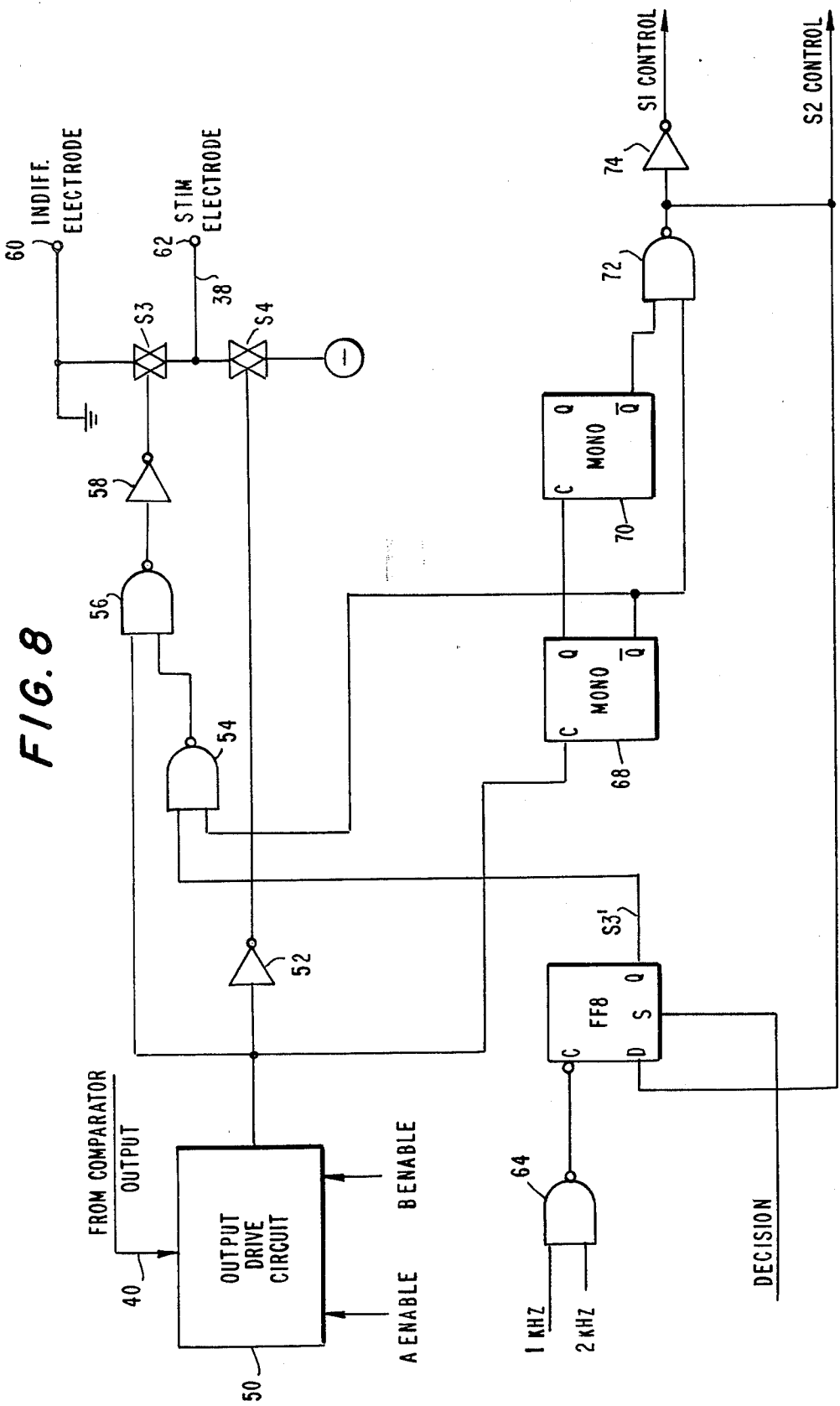

The circuit of FIG. 5 includes three transmission gates S1, S2 and S3. Gates S1 and S2 are controlled by the S1 ENABLE (FIG. 6) and S2 ENABLE (FIG. 7) signals to be described below. Gate S3 is connected between the stimulating electrode and ground, and it is shown in FIG. 8 as well as in FIG. 5. As shown in FIG. 8, this gate is controlled by the output of inverter 58. The three gates, or switches, A, B and C of FIG. 5 are controlled by the three respective "ENABLE" signals shown at the bottom of FIG. 7. The six control signals are derived by the logic circuit, the logic circuit operating in accordance with the bit stream which appears at the output of comparator 34 of FIG. 5. The manner in which the control signals are derived will be considered below, but first the circuit of FIG. 5 will be described.

Transistor N1 biases transistor N2 to deliver a constant current. The current flows down through one of gates A, B or C, and through the connected one of transistors N3, N4 or N5. As will become apparent below, only one of gates A or B may be on at any given time. Whenever neither gate is on, gate C is on. In this way, current always flows through the circuit. The same current flows constantly through transistor N2, but it is steered differently depending upon which of gates A, B or C is on at any particular time. Gate C is provided simply to ensure that there is a current flowing whenever one of gates A or B turns on (at which time gate C turns off), so that there is no delay in building up the current. Transistor N2 is arranged in a cascode configuration to ensure that the same magnitude current flows through gates A, B and C, no matter which gate is on and independent of the potentials across the elements to which the gate is connected.

Whenever gate A is on, gate S2 is also on but gate S1 is off. Consequently, current flows from ground through gate S2, to the left through capacitor 30, and down through transistor N3, gate A and transistor N2. As will become apparent below, gate S2 is turned on before gate A is turned on, and it is turned off after gate A has turned off. Consequently, current can flow from right to left through capacitor 30 for the entire duration of the conduction of gate A.

In order to control a comparable current flow from left to right through capacitor 30, gates S1, S3 and B must be on simultaneously (while gate S2 is off). In this case, the current flows from ground through gates S3 and S1, the capacitor, transistor N4, gate B and transistor N2. Gates S1 and S3 are turned on before gate B is turned on, and they are turned off after gate B has turned off, as will be described below. Consequently, gate B conducts current during the entire time that it is held on. (Alternatively, the current can flow through the electrode rather than gate S3.)

The bottom of gate S2 is shown as being connected to ground in FIG. 5. Actually, the bottom of the gate is not connected to ground, and instead is connected to the output of comparator 34, as symbolized by the dashed line 36. It must be understood that for correct circuit operation the comparator must have no hysteresis and the combination of amplifier and comparator must be stable with gate S2 closed giving a unity gain configuration. The reason for the dashed-line connection will be described below, but it is easier to understand the circuit operation if the bottom of gate S2 is considered to be connected to ground as shown in FIG. 5.

The logic circuit first "samples" the input signal at the stimulating electrode in order to determine the direction in which current should flow through capacitor 30. During the sampling time, gates A and B are both off, and consequently gate C is on since it is on whenever both of the other two gates are off. The constant current delivered by transistor N2 flows through transistor N5 and gate C, but otherwise has no effect on the circuit operation.

During the sampling interval, gate S1 is held on while gates S2 and S3 are held off, i.e., the S1 ENABLE signal on FIG. 6 is high, the S2 ENABLE signal on FIG. 7 is low, and the S3' signal on FIG. 8 is high. The difference between the potential of the input signal and that across capacitor 30 appears at the plus input of amplifier 32. Assuming that capacitor 30 is initially discharged and the input signal is positive, the output of comparator 34 goes low to indicate an increasing input signal. During the sampling, capacitor 30 does not actually charge or discharge because it is connected to the plus input of operational amplifier 32 which has a very high impedance. But after the sampling the logic circuit, which has registered the negative output at comparator 34 indicating an increasing signal at the stimulating electrode, turns gates S1, S3 and B on; gates S2 and A remain off. Consequently, current flows from left to right through capacitor 30 to charge it. The same operation takes place following successive samplings until capacitor 30 has charged to the level of the input signal.

On the other hand, whenever the input signal falls in potential to a level below that of capacitor 30, the potential at the plus input of amplifier 32 will be negative when a sample is taken and the resulting bit which is generated at the output of comparator 34 will be positive. The logic circuit now controls turn-on of gates S2 and A. (As will be described below, gate S3 is also held on but it has no effect on the current flow because gate S1 is held off.) For as long as gate A is held on, current flows through gate S2, to the left through capacitor 30, and down through transistor N3, gate A and transistor N2. The capacitor is thus discharged. This process continues, with capacitor 30 being charged or discharged during each cycle in accordance with the level of the output of comparator 34 when the preceding sample was taken. Gates A and B are turned on, when they are, for the same interval; since the same constant current source N2 is used to control current flow through capacitor 30 in both directions, it is apparent that the capacitor is charged or discharged an equal amount during each cycle and no error is introduced due to the use of different magnitude current sources for charging and discharging the capacitor.

If the input signal is constant, once capacitor 30 stabilizes alternate bit values of 0 and 1 appear at the output of comparator 34, and capacitor 30 is alternately charged and discharged.

As will be described below, following the generation of a pacing pulse all of gates S1, S2 and S3 are turned on. Gate S3 is turned on for 5 milliseconds and shorts the two electrodes to each other, since the indifferent electrode is grounded as shown in FIG. 8. The reason for doing this is to allow most of the charge stored in the heart tissue to be recovered. While most of the charge stored in the electrode/electrolyte interfaces can be recovered during these five milliseconds, some charge remains and the potential at the stimulating electrode may be of the order of 0.5 volts by the time gate S3 is turned off. While 0.5 volts is considerably lower than a typical 5-volt pacing pulse, capacitor 30 must charge or discharge until its potential equals this initial voltage before tracking of the physiological signal to be monitored can begin. It may taken several tens of milliseconds for the capacitor to recover, and the system logic may ignore the resulting bit stream at the output of comparator 34 during this interval. In a practical pacer, a longer refractory period is usually provided anyway, in order that the after-effects of the pacing pulse can be ignored; thus to have the logic circuit ignore initial bit values at the output of comparator 34 is not out of the ordinary. But we provide a mechanism to further speed up the capacitor recovery.

During the time that gate S3 is held on following the generation of a pacing pulse, gates S1 and S2 are also held on. However they are held on for an extra 1-2 milliseconds to speed up the capacitor recovery, i.e., by providing a direct path which connects the capacitor between the input terminal and ground.

But even perfect recovery of the capacitor is not sufficient. Any practical operational amplifier or comparator has an offset voltage, e.g., in the 25-millivolt range for a typical CMOS operational amplifier, which is in effect a built-in threshold voltage. The output of the comparator does not change until the input reaches the offset voltage. In other words, even though the plus input of amplifier 32 may have a potential of zero following the recovery process, as far as the overall comparator is concerned this is not the "decision point" for the actual threshold of the device. It is for this reason that the bottom end of gate S2 is connected to the output of comparator 34 instead of being returned to ground as actually shown in FIG. 5. The feedback from the output of the comparator to the input actually charges or discharge capacitor 30 so that the plus input of amplifier 32 is biased to the offset potential of the comparator. In other words, the negative feedback compensates for the offset by charging or discharging the capacitor. This is a standard technique known in the art for compensating the effect of the offset voltage, and the standard precautions concerning stability must be observed.

With this general description of the operation of the circuit of FIG. 5 in mind, the logic for controlling the gate openings and closings will now be described. The logic itself is shown in FIGS. 6 and 7, and much of the circuit operation is depicted in the timing waveforms of FIGS. 10 and 11.

A 4-kHz clock signal is applied to the CLK input of flip-flop FF1. Flip-flops FF1, FF2 and FF3 are configured as divide-by-two counters so as to generate 2-kHz, 1-kHz and 500-Hz clock signals. It is these clock signals which determine the operations of gates S1, S2 and S3, and gates A, B and C, in order to control sampling and charging/discharging of capacitor 30. (Gates S1, S2 and S3 have their operations further controlled when a pacing pulse is generated, but this is not under direct control of the clock signals and will be described below.) The first four waveforms on FIG. 10 depict the original and the three derived clock signals.

Gate G2 is controlled by the two highest clock frequencies, and its output is depicted as the fifth waveform on FIG. 10. Gate G3 is controlled by the two lowest clock signals and its output, $\overline{\text{DECISION}}$, is fed to the CLK input of flip-flop FF5. The same signal is inverted by inverter I15, and thus the output of the inverter is the DECISION signal. This signal is depicted as the sixth waveform on FIG. 10. Since it is the DECISION signal which is extended to the CLK input of flip-flop FF5, and the flip-flop is clocked on a rising edge, the flip-flop is clocked on the falling edge of the DECISION signal depicted on FIG. 10. The output from comparator 34 on FIG. 5, after inversion by inverter I13, is latched in flip-flop FF5 on each falling edge of the DECISION signal. It is the state of flip-flop FF5 which determines whether current flow through capacitor 30 on FIG. 5 should be controlled by gates S2 and A, or gates S1 and B. As described above, gate S3 must be on with gates S1 and B to control current flow from left to right through capacitor 30. In actuality, gate S3 is operated even when current flow is in the opposite direction because at such time gate S1 is off and conduction through gate S3 has no effect on the capacitor. Gate S3 must be off, however, during sampling so as not to short the input terminal, at which time gate S1 is on and gate S2 is off.

Gate G4 is controlled by the inverse of the two clock signals which control gate G3. The signal at the output of inverter I4 is different from the DECISION signal, however, because it is controlled by different outputs of flip-flops FF2 and FF3; it has the same mark/space ratio but is slightly delayed. The I4 signal is combined in gate G14 with the signal at the output of gate G2, after inversion of the latter by inverter I3. The signal at the output of gate G14 is inverted by inverter I14, and the inverted signal serves as the clock signal for flip-flop FF6. The signal at the output of inverter I14 is depicted as the last waveform in FIG. 10, and it will be observed that flip-flop FF6 is clocked shortly after a sample is first latched in flip-flop FF5 on the falling edge of the DECISION signal. It is the state of flip-flop FF6 which actually controls the state of gate S1, since the S1 ENABLE signal is derived from the Q output of flip-flop FF6.

Gates G15, G17 and G18 provide a short pulse equal to the switching times of the three devices. The S1 CONTROL signal is normally high so that it has no effect on gate G16. (The S1 CONTROL signal goes low to control the turn-on of gate S1 only after the generation of a pacing pulse, as will be described below.) The net result is that after a short delay, each rising edge of the DECISION signal results in a positive step at the set input of flip-flop FF6; the Q output goes high to turn on gate S1. As described above, gate S1 is turned on during each sampling interval so that the potential at the stimulating electrode can be sensed by the comparator. By turning on gate S1 at the beginning of each DECISION pulse, as shown in the second waveform of FIG. 11, but latching the comparator output in flip-flop FF5 only following the end of each DECISION pulse, almost the full duration of the DECISION pulse is available for the comparator to determine the direction in which current should flow through capacitor 30 in order that the capacitor voltage track the potential at the stimulating electrode.

Although the derivation of the S1 CONTROL signal will be described below, it should be noted that if this signal is held low flip-flop FF6 has its set input held high so that the S1 ENABLE signal remains high as well. This is how gate S1 is held on following the generation of a pacing pulse. Once the S1 CONTROL signal goes high again, the state of flip-flop FF6 is controlled by the values of succeeding samples.

Flip-flop FF7 controls the state of gate S2. The S2 CONTROL signal, when high, is used to hold the flip-flop in the set state so that gate S2 is held on following the generation of a pacing pulse, as will be described below. Except for this pacing-pulse control, flip-flop FF7 controls gate S2 depending upon the sample value stored in flip-flop FF5, just as flip-flop FF6 uses the same sample value to control gate S1. It is the $\bar{Q}$ output of flip-flop FF5, connected to the D input of flip-flop FF7, which controls the state of the latter flip-flop just as the Q output connection of flip-flop FF5 to the D input of flip-flop FF6 controls the state of this latter flip-flop. With respect to flip-flop FF7, several gates operate on the various clock signals to derive a reset signal at the output of inverter I12 and a clock signal at the output of inverter I8. Both of these signals are shown in the waveforms of FIG. 11.

FIG. 11 also depicts three waveforms which make clear why the S1 and S2 gate operations are mutually exclusive (except following a pacing pulse). The waveform labelled Q on FIG. 11 represents the state of flip-flop FF5. The waveform labelled S1 is the S1 ENABLE signal, i.e., it represents the state of flip-flop FF6. The waveform labelled S2 is the S2 ENABLE signal, i.e., it represents the state of flip-flop FF7. It is assumed in FIG. 11 that the first sample derived by the comparator is a 0 so that the output of inverter I13 is high. It is further assumed that the next sample is a 1, so that the output of inverter I13 is low. No matter what the state of flip-flop FF5 prior to the falling edge of the first DECISION pulse (as symbolized by the shading in the Q waveform of FIG. 11), the first falling edge of the DECISION pulse sets flip-flop FF5 in the 1 state and its Q output goes high. The flip-flop remains in this state until the falling edge of the next DECISION pulse, at which time the Q output goes low since the output of inverter I13 is now low for the new sample.

When charging capacitor 30, gate S1 is on. It must also be on during sampling, i.e., starting with the rising edge of the DECISION pulse. There is no reason to turn the gate off between these two events. On the other hand, gate S1 is off during discharging of capacitor 30 and it must be turned on for sampling purposes at the start of the DECISION pulse. The left side of the S1 waveform on FIG. 11 is shown shaded since no assumption is made as to the initial state of flip-flop FF6. But on the rising edge of the first DECISION pulse, as described above, flip-flop FF6 is set and the S1 signal goes high. When inverter I14 clocks the flip-flop, the state of flip-flop FF5, represented by the Q waveform on FIG. 11, is transferred to flip-flop FF6. In the case of the first sample depicted in the waveforms, flip-flop FF6 simply remains set in the 1 state. Similarly, the rising edge of the next DECISION pulse, which would otherwise set the flip-flop, has no effect since the flip-flop is already set. It is only the second I14 clock pulse which resets the flip-flop since the second sample has resulted in the Q output of flip-flop FF5 being low.

Whenever the output of inverter I12 goes high, flip-flop FF7 is reset and the S2 ENABLE signal goes low. The left side of the S2 waveform is shaded on FIG. 11 since no assumption is made as to the initial state of flip-flop FF7, but the signal is low starting with the rising edge of the I12 reset pulse. The flip-flop is clocked on the rising edge of each pulse generated by inverter I8, and the state of the flip-flop is determined by the signal at the $\bar{Q}$ output of flip-flop FF5 (the inverse of which is shown as the Q waveform on FIG.

11). Since the first sample stored in flip-flop FF5 is a 1, the S2 waveform in FIG. 11 remains low when the first clock pulse from inverter I8 is generated. Since the second sample stored in flip-flop FF5 is a 0, flip-flop FF7 is set in the 1 state when the second clock pulse from inverter I8 is generated, as represented by the S2 waveform on FIG. 11. The flip-flop is reset once again, on the rising edge of the next pulse generated by inverter I12.

There are several important things to note about the S1 and S2 waveforms on FIG. 11. The first is that they are never over-lapping (except following the generation of a pacing pulse when they are both high, as will be described below). Only one of the two gates should be on at any one time to control current flow through capacitor 30, in order to charge or discharge it. While the S2 gate is always turned off by a reset pulse applied to flip-flop FF7 by inverter I12, there is no automatic turn-off of gate S1. This gate is turned off only if the sample stored in flip-flop FF5 requires that the gate be turned off. Otherwise, the gate may remain on continuously. This is because the gate must be on both during sampling and during charging of capacitor 30 when current flows from left to right through it. There is no reason to turn the gate off unless current must flow through capacitor 30 in the opposite direction. Gate S2 is always turned off however, after a discharge current from right to left flows through the capacitor, because this gate must be off when the next sample is taken.

It was emphasized above that capacitor 30 should be charged or discharged by constant steps following the taking of each sample. The fact that gates S1 and S2 are held on for different durations is of no moment because current actually flows through capacitor 30 only when one of gates A or B is turned on. (Although gate S1 remains on during the sampling period and even during other portions of each overall cycle when a charging or discharging current through capacitor 30 is not actually required, this is of no importance because no significant current can actually flow through capacitor 30 unless one of gates B or S2 is on; it is to be recalled that the plus input of amplifier 32 has an input current much less than a nanoampere.) Equal currents are made to flow in the two directions through capacitor 30 when gate S1 or S2 is on by causing gates A and B to turn on for equal durations. It is in this manner that the same current from current source N2 charges or discharges the capacitor for the same time interval during each cycle.

Referring to the A and B waveforms on FIG. 11, which represent the A ENABLE and B ENABLE signals at the bottom of FIG. 7, it will be noted that each pulse has the same duration when it is generated. It should further be noted that each pulse occurs while the respective S1 or S2 signal is high respectively; as described above, gate S1 or S2 is on before the turn-on of the respective one of gates B or A, and gate S1 or S2 is not turned off until after the turn-off of the respective one of gates B or A. Which of gates A or B is turned on is controlled by the state of the flip-flop FF4. The state of the flip-flop is determined by the $\overline{Q}$ output of flip-flop FF5, that is, the value of the last sample. The remaining logic on FIG. 7 simply controls the clocking of flip-flop FF4, as well as the pulsing high of one of the A ENABLE or B ENABLE lines during each overall cycle. The logic also controls the C ENABLE signal to be high only when both of the A ENABLE and B ENABLE signals are low, so that current source N2 always conducts a constant current, even when capacitor 30 is not being charged or discharged. The A and B waveforms on FIG. 11 can be derived by drawing the intervening controlling waveforms, as is known in the art. Referring to the basic clock waveforms on FIG. 10, and the A and B waveforms on FIG. 11, it will be noted that overall cycles occur at a 500-Hz rate, with the capacitor being charged or discharged for 0.5 milliseconds during each overall cycle.

FIG. 9 depicts a very simple illustrative circuit for actually determining the occurrence of a cardiac event of interest from the samples derived by the delta modulator circuit. The A ENABLE or B ENABLE line is pulsed high during each cycle. These two signals are extended through OR gate 82 and delay 84 (to allow the data input to settle before clocking) to the clock input of shift register 80. Thus the shift register is clocked once during each overall cycle. The data input to the shift register is connected to the A ENABLE signal, although the B ENABLE signal could be used instead since one is the inverse of the the other. The net result is that the four last samples are always represented in the successive stages of the shift register. Gates 86 and 88 detect respectively the presence of four 0 samples or four 1 samples, and OR gate 89 pulses its output conductor 90 in either case. What this means is that four successive samples of the same value, representing either a rising or falling segment of the electrogram signal, is treated as a ventricular contraction to control the pacer timing.

Since the electrogram signal has rising and falling portions corresponding to each ventricular contraction, it is possible for conductor 90 to be pulsed twice for each ventricular contraction. This is of no moment, however, because conventional pacer systems are designed to ignore sensed signals within a refractory period following the detection of a ventricular contraction, and the second pulsing of conductor 90 would invariably occur during this refractory period.

It is anticipated that more sophisticated schemes can be developed for processing the sample stream which is generated. The scheme of FIG. 9, while simple, is nevertheless satisfactory. More sophisticated schemes, especially those used for dual-chamber pacers, may require samples to be taken at a rate faster than the 500-Hz rate of the illustrative embodiment of the invention. But this simply requires the use of a faster clock instead of the 4-kHz clock which is illustrated.

The step size, that is, the incremental change in potential of capacitor 30 during each overall cycle, is also a factor to be considered. If the magnitude of the current delivered by transistor N2 is too high, the capacitor potential might even overshoot on each sample and tracking of the input signal would not be possible. All that would happen would be the generation of a succession of alternating 0's and 1's. The step size must be small enough to ensure that a succession of bit samples of only one value results as the capacitor potential "catches up" to the input signal; it is by generating a sample sequence of this type that an event of interest can actually be determined.

But if the sampling rate is increased, and even with a relatively small step size, it is possible for a cardiac event of interest to be represented by a sequence of samples which while not exclusively of one value, nevertheless has many more samples of one value than the other. In such a case, what might be required is some kind of majority logic, that is, the detection of a predetermined number of samples of one particular value among the last group of samples, with the number of samples in the group being some number higher than that required for a majority decision.

Rather than to provide fixed patterns or majority decisions as recognition criteria, adaptive systems are also possible. In such a case, one or more previously recognized signals may alter the predetermined pattern which is next used as the recognition criterion.

It is also to be understood that more complicated recognition schemes such as those under consideration can probably best be implemented in firmware rather than hardware, especially since this would even facilitate the use of external programmers to modify the decision logic depending upon patient needs. It is also possible to completely eliminate the need for the implanted pacer to make any logic decisions. With the generation of a simple bit stream in the manner described, a telemetry system could be utilized by which the sample values are transmitted to an external monitor which would then make the appropriate decision and transmit a signal back to the pacer to control the generation of a pacing pulse.

The remainder of the overall pacer circuit is shown in FIG. 8. Referring back to FIG. 5, it will be seen that gate S3 is connected between the stimulating electrode and ground. This same gate is shown in FIG. 8 connected between the stimulating electrode 62 and the indifferent electrode 60, since the latter is grounded. One purpose of the gate is to short the two electrodes to each other following the generation of a pacing pulse in order to recover most of the charge stored in the electrode/electrolyte interfaces. The other purpose of the gate is to connect gate S1 to ground when capacitor 30 is to be charged, although capacitor 30 may be charged through the electrode itself. The circuitry in FIG. 8 develops a signal for turning on gate S3, as well as the S1 CONTROL and S2 CONTROL signals for turning on gates S1 and S2 simultaneously following the generation of a pacing pulse, as described above.

Gate S4 on FIG. 8 simply connects the stimulating electrode to the negative supply. This gate is turned on whenever a pacing pulse is to be generated. (Alternatively, a charge storage capacitor could be utilized as is standard in the art, with the capacitor discharging through the gate into the electrode when a pacing pulse is required. The details of this standard configuration are not necessary for an understanding of the invention and, accordingly, what is depicted is simply the use of a gate S4 for controlling the connection of the battery to the stimulating electrode.) An inverter 52 is shown as driving gate S4 since a negative pulse is generated by drive circuit 50 when a pacing pulse is required, the duration of the output pulse from circuit 50 being equal to and controlling the duration of the pacing pulse.

Flip-flop FF8 controls the turning on of gate S3. The three signals which control the state of the flip-flop are applied to the inputs of gate 64 and to the set input of the flip-flop, with all three signals being derived from the logic circuit of FIGS. 6 and 7. Output drive circuit 50, which determines when a pacing pulse is to be generated and controls it by pulsing its output low, is provided with three inputs—the comparator output, and the A ENABLE and B ENABLE signals. If the decision logic of FIG. 9 is actually used in output drive circuit 50 of FIG. 8, then only the A ENABLE and B ENABLE signals are required as inputs. The input from the comparator output is shown because it may be required in more sophisticated implementations, particularly those involving dual-chamber pacing where a greater number of decisions of different types have to be made.

Output drive circuit 50 operates in a conventional manner to generate negative pulses at its output in order to control the generation of pacing pulses. Typically, the output drive circuit generates pulses at 800-millisecond intervals. It is when a ventricular contraction is detected, for example, by a circuit such as that shown in FIG. 9, that the next pacing pulse is inhibited and a new 800-millisecond timing interval begins. Whenever a pacing pulse is generated, the input of gate 56 connected to the output of circuit 50 is held low so that the gate output goes high. Inverter 58 thus holds gate S3 off since the two electrodes should not be shorted together while a pulse is being generated.

Monostable multivibrator 68 is triggered at the trailing (rising) edge of each pulse generated by circuit 50. The $\overline{Q}$ output of the multivibrator goes low so that the outputs of gates 54 and 72 both go high. As soon as the Q output of multivibrator 68 goes high, monostable multivibrator 70 is also triggered and its $\overline{Q}$ output goes low. Since this output is also connected to an input of gate 72, it further causes the output of gate 72 to remain high. Multivibrator 68 has a timing interval of 5 milliseconds and multivibrator 70 has a timing interval of 6–7 milliseconds. Consequently, the output of gate 72 remains high for 6–7 milliseconds starting with the termination of the pacing pulse. The high potential on the S2 CONTROL lead causes gate S2 to be turned on as described above. The same high potential at the output of gate 72 is inverted by inverter 74 to provide a low potential on the S1 CONTROL conductor during the same time interval; as described above, this causes the S1 gate to remain on.

When multivibrator 68 is first triggered at the trailing edge of the pacing pulse, the output of gate 54 goes high. Thus one input of gate 56 is high. Since the pacing pulse has terminated, the other input of gate 56 is also high. Consequently, its output goes low for the five milliseconds that the $\overline{Q}$ output of flip-flop 68 remains low, and the output of inverter 58 goes high for 5 milliseconds to hold on gate S3. It is during these five milliseconds that the two electrodes are shorted to each other to recover stored charge. As described above, the S1 and S2 gates are held on for an additional 1–2 milliseconds in order to allow capacitor 30 to rapidly charge in accordance with the potential which remains on the stimulating electrode at the end of the charge dissipation interval.

As described above with reference to FIG. 5, gate S3 must be turned on not only following the generation of a pacing pulse, but also when gate S1 and gate B are on to control the charging of capacitor 30, unless capacitor 30 is charged through the electrode. The current in this case flows from ground through gates S3 and S1. When gates S2 and A control the discharge of capacitor 30, there is no need for gate S3 to be on since gate S1 is off. Nevertheless, there is no reason for gate S3 not to be turned on, and it is simpler from a control standpoint for gate S3 to turn on during every cycle whether the capacitor is being charged or discharged.

Whenever the DECISION signal goes high, flip-flop FF8 on FIG. 8 is set and its Q output goes high. The Q output of the flip-flop is the S3' signal which serves as one input to gate 54, the S3' waveform being shown at the bottom of FIG. 11. Gate 64 has the 1-kHz and 2-kHz clock signals as its inputs, and flip-flop FF8 is clocked shortly prior to the time during each overally cycle that one of the A ENABLE or B ENABLE signals goes high. Consequently, for as long as the output of gate 72 is low, and because of its connection to the D input of flip-flop FF8, the flip-flop is reset with the S3' signal going low each time that the flip-flop is clocked. In the absence of the generation of a pacing pulse, the output of gate 72 is indeed low since both of its inputs are high. It can thus be seen that the S3' signal goes low during each cycle shortly before the A ENABLE or B ENABLE signal goes high, and it goes high again after the A ENABLE or B ENABLE pulse has terminated. Consequently, the S3' signal is low so as to bracket each of the A ENABLE or B ENABLE pulses. For as long as the S3' signal is low, the output of gate 54 is high. Since both inputs to gate 56 are high in the absence of the generation of a pacing pulse, the output of the gate is low and inverter 58 causes gate S3 to remain on as described above. Gate S3 is thus held off when a pacing pulse is being generated, it is held on for five milliseconds following the generation of each pacing pulse, and it is also held on while capacitor 30 is being charged or discharged as it tracks the input signal. Because the S3' signal is high from the start of the DECISION pulse (just before gate S1 is turned on to permit sampling) until the end of the DECISION gate (when a sample is latched in flip-flop FF5), gates S3 is held off during the entire sampling period—as it must be in order not to short the electrode whose potential is to be sampled.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. An implantable heart pacer comprising electrode means, means for applying a stimulating current pulse to said electrode means, means for sensing an electrical signal on said electrode means representative of cardiac activity, and means for controlling operation of said current pulse applying means in accordance with the operation of said sensing means, characterized by said sensing means including means for generating a continuous sequence of bit samples, the two stages of said bit samples representing changes in respective opposite directions in the sensed electrical signal, and means for analyzing said continuous bit sample sequence to determine the occurrence of a predetermined type of cardiac activity to control operation of said current pulse applying means in accordance therewith, and wherein said bit sample generating means operates directly on the sensed electrical signal without any prior filtering in the frequency domain and includes capacitor means, means for charging said capacitor means, means for discharging said capacitor means, means for periodically comparing the potential across said capable means with the potential of the sensed electrical signal to derive bit samples the state of each of which represents the result of the most recent comparison, means for operating either said charging means or said discharging means in accordance with the state of each bit sample to control the potential across said capacitor means to track the potential of the sensed electrical signal, a constant current source, means for causing and constant current source to be utilized by both of said charging and discharging means to effect equal but opposite increments in the potential of said capacitor means independent of which of said charging or discharging means is operated in accordance with the state of each bit sample, means for holding said charging and discharging means unoperated during operation of said comparing means and for always holding said constant current source operated, and further including means for steering current from said constant current source away from said capacitor means whenever neither of said charging and discharging means is operated.

2. An implantable heart pacer in accordance with claim 1 wherein said capacitor means is connected in series between said electrode means and said comparing means, and each of said charging and discharging means includes a set of switches connected to both sides of said capacitor means for delivering current from said constant current source to said capacitor means, the two sets of switches being connected to said constant current source so as to deliver currents to said capacitor means in respective opposite directions.

3. An implantable heart pacer in accordance with claim 2 wherein a first switch in one set is connected to one side of said capacitor means and a first switch in the other set is connected to the other side of said capacitor means, and further including means for operating both of said switches simultaneously for a brief interval following the application of a stimulating current pulse to said electrode means to allow the potential across said capacitor means to rapidly recover to the potential of the sensed electrical signal.

4. An implantable heart pacer in accordance with claim 3 further including means for shorting said electrode means briefly following the application of a stimulating current pulse thereto to facilitate recovery of any charge stored in body tissues as a result of the stimulating current pulse, and means for causing said electrode means to be thus shorted for a shorter interval than that during which both of said first switches are operated simultaneously.

5. An implantable heart pacer in accordance with claim 4 wherein said analyzing means includes means for determining the occurrence of said predetermined type of cardiac activity responsive to the generation of a predetermined number of successive bit samples of the same state.

6. An implantable heart pacer comprising electrode means, means for applying a stimulating current pulse to said electrode means, means for sensing an electrical signal on said electrode means representative of cardiac activity, and means for controlling operation of said current pulse applying means in accordance with the operation of said sensing means, characterized by said sensing means including means for generating a continuous sequence of bit samples, the two states of said bit samples representing changes in respective opposite directions in the sensed electrical signal, and means for analyzing said continuous bit sample sequence to determine the occurrence of a predetermined type of cardiac activity to control operation of said current pulse applying means in accordance therewith, and wherein said bit sample generating means includes capacitor means, means for charging said capacitor means, means for discharging said capacitor means, means for periodically comparing the potential across said capacitor means with the potential of the sensed electrical signal to derive bit samples the state of each of which represents the result of the most recent comparison, means for operating either said charging means or said discharging means in accordance with the state of each bit sample to control the potential across said capacitor means to track the potential of the sensed electrical signal, a constant current source, means for causing said constant current source to be utilized by both of said charging and discharging means to effect equal but opposite increments in the potential of said capacitor means independent of which of said charging or discharging means is operated in accordance with the value of each bit sample, means for holding said charging and discharging means unoperated during operation of said comparing means and for always holding said constant current source operated, and means for steering current from said constant current source away from said capacitor means whenever neither of said charging and discharging means is operated.

7. An implantable heart pacer comprising electrode means, means for applying a stimulating current pulse to said electrode means, means for sensing an electrical signal on said electrode means representative of cardiac activity, and means for controlling operation of said current pulse applying means in accordance with the operation of said sensing means, characterized by said sensing means including means for generating a continuous sequence of bit samples, the two states of said bit samples representing changes in respective opposite directions in the sensed electrical signal, and means for analyzing said continuous bit sample sequence to determine the occurrence of a predetermined type of cardiac activity to control operation of said current pulse applying means in accordance therewith, and wherein said bit sample generating means includes capacitor means, means for charging said capacitor means, means for discharging said capacitor means, means for periodically comparing the potential across said capacitor means with the potential of the sensed electrical signal to derive bit samples the state of each of which represents the result of the most recent comparison, means for operating either said charging means or said discharging means in accordance with the state of each bit sample to control the potential across said capacitor means to track the potential of the sensed electrical signal, said capacitor means being connected in series between said electrode means and said comparing means, and each of said charging and discharging means including a set of switches connected to both sides of said capacitor means for delivering current from said constant current source to said capacitor means, the two sets of switches being connected to said constant current source so as to deliver currents to said capacitor means in respective opposite directions.

8. An implantable heart pacer in accordance with claim 7 wherein a first switch in one set is connected to one side of said capacitor means and a first switch in the other set is connected to the other side of said capacitor means, and further including means for operating both of said switches simultaneously for a brief interval following the application of a stimulating current pulse to said electrode means to allow the potential across said capacitor means to rapidly recover to the potential of the sensed electrical signal.

9. An implantable heart pacer in accordance with claim 8 further including means for shorting said electrode means briefly following the application of a stimulating current pulse thereto to facilitate recovery of any charge stored in body tissues as a result of the stimulating current pulse, and means for causing said electrode means to be thus shorted for a shorter interval than that during which both of said first switches are operated simultaneously.

10. An implantable heart pacer in accordance with claim 9 wherein said analyzing means includes means for determining the occurrence of said predetermined type of cardiac activity responsive to the generation of a predetermined number of successive bit samples of the same state.

11. An implantable heart pacer comprising electrode means, means for applying a stimulating current pulse to said electrode means, means for sensing an elelctrical signal on said electrode means representative of cardiac activity, and means for controlling operation of said current pulse applying means in accordance with the operation of said sensing means, characterized by said sensing means including means for generating a continuous sequence of digital samples representative of the sensed electrical signal, said digital sample generating means operating directly on the sensed electrical signal without any prior filtering in the frequency domain, and means for analyzing said continuous digital sample sequence to determine the occurrence of a predetermined type of cardiac activity to control operation of said current pulse applying means in accordance therewith; said digital sample generating means including capacitor means, means for charging said capacitor means, means for discharging said capacitor means, means for periodically comparing the potential across said capacitor means with the potential of the sensed electrical signal to derive digital samples the state of each of which represents the result of the most recent comparison, means for operating either said charging means or said discharging means in accordance with the state of each digital sample to control the potential across said capacitor means to track the potential of the sensed electrical signal, a constant current source, means for causing said constant current source to be utilized by both of said charging and discharging means to effect opposite increments in the potential of said capacitor means independent of which of said charging or discharging means is operated in accordance with the value of each digital sample, means for holding said charging and discharging means unoperated during operation of said conparing means and for always holding said constant current source operated, and means for steering current from said constant current source away from said capacitor means whenever neither of said charging and discharging means is operated.

12. An implantable heart pacer comprising electrode means, means for applying a stimulating current pulse to said electrode means, means for sensing an electrical signal on said electrode means reprsentative of cardiac activity, and means for controlling operation of said current pulse applying means in accordance with the operation of said sensing means, characterized by said sensing means including means for generating a continuous sequence of digital samples representative of the sensed electrical signal, said digital sample generating means operating directly on the sensed electrical signal without any prior filtering in the frequency domain, and means for analyzing said continuous digital sample sequence to determine the occurrence of a predetermined type of cardiac activity to control operation of said current pulse applying means in accordance therewith; said digital sample generating means including capacitor means, means for charging said capacitor means, means for discharging said capacitor means, means for periodically comparing the potential across said capacitor means with the potential of the sensed electrical signal to derive digital samples the state of each of which represents the result of the most recent comparison, and means for operating either said charging means or said discharging means in accordance with the state of each digital sample to control the potential across said capacitor means to track the potential of the sensed electrical signal, and wherein said capacitor means is connected in series between said electrode means and said comparing means, and each of said charging and discharging means includes a set of switches connected to both sides of said capacitor means for delivering current to said capacitor means, the two sets of switches being connected so as to deliver current to said capacitor means in respective opposite directions.

13. An implantable heart pacer in accordance with claim 12 wherein a first switch in one set is connected to one side of said capacitor means and a first switch in the other set is connected to the other side of said capacitor means, and further including means for operating both of said switches simultaneously for a brief interval following the application of a stimulating current pulse to said electrode means to allow the potential across said capacitor means to rapidly recover to the potential of the sensed electrical signal.

14. An implantable heart pacer in accordance with claim 13 further including means for shorting said electrode means briefly following the application of a stimulating current pulse thereto to facilitate recovery of any charge stored in body tissues as a result of the stimulating current pulse, and means for causing said electrode means to be thus shorted for a shorter interval than that during which both of said first switches are operated simultaneously.

15. An implantable heart pacer in accordance with claim 14 wherein said analyzing means includes means for determining the occurrence of said predetermined type of cardiac activity responsive to the generation of a predetermined number of successive digital samples which have a predetermined pattern.

16. An implantable medical device comprising electrode means and means for sensing an electrical signal on said electrical means representativee of physiological activity, characterized by said sensing means including means operating directly on the sensed electrical signal without any prior filtering in the frequency domain for generating a continuous sequence of bit samples, the two states of said bit samples representing changes in respective opposite directions in the sensed electrical signal, said bit sample generating means including capacitor means, means for charging said capacitor means, means for discharging said capacitor means, means for periodically comparing the potential across said capacitor means with the potential of the sensed electrical signal to derive bit samples the state of each of which represents the result of the most recent comparison, means for operating either said charging means or said discharging means in accordance with the state of each bit sample to control the potential across said capacitor means to track the potential of the sensed electrical signal, a constant current source, means for causing said constant current source to be utilized by both of said charging and discharging means to effect equal but opposite increments in the potential of said capacitor means independent of which of said charging or discharging means is operated in accordance with the state of each bit sample, means for holding said charging and discharging means unoperated during operation of said comparing means and for always holding said constant current source operated, and means for steering current from said constant current source away from said capacitor means whenever neither of said charging and discharging means is operated.

17. An implantable medical device comprising electrode means and means for sensing an electrical signal on said electrode means representative of physiological activity, characterized by said sensing means including means operating directly on the sensed electrical signal without any prior filtering in the frequency domain for generating a continuous sequence of bit samples, the two states of said bit samples representing changes in respective opposite directions in the sensed electrical signal, said bit sample generating means including capacitor means, means for charging said capacitor means, means for discharging said capacitor means, means for periodically comparing the potential across said capacitor means with the potential of the sensed electrical signal to derive bit samples the state of each of which represents the result of the most recent comparison, means for operating either said charging means or said discharging means in accordance with the state of each bit sample to control the potential across said capacitor means to track the potential of the sensed electrical signal, said capacitor means being connected in series between said electrode means and said comparing means, and each of said charging and discharging means including a set of switches connected to both sides of said capacitor means for delivering current to said capacitor means, the two sets of switches being connected so as to deliver currents to said capacitor means in respective opposite directions.

18. An implantable medical device in accordance with claim 17 wherein a first switch in one set is connected to one side of said capacitor means and a first switch in the other set is connected to the other side of said capacitor means, and further including means for applying a stimulating signal to said electrode means, and means for operating both of said switches simultaneously for a brief interval following the application of a stimulating signal to said electrode means to allow the potential across said capacitor means to rapidly recover to the potential of the sensed electrical signal.

19. An implantable medical device in accordance with claim 18 further including means for shorting said electrode means briefly following the application of a stimulating current signal thereto to facilitate recovery of any charge stored in body tissues as a result of the stimulating current signal, and means for causing said electrode means to be thus shorted for a shorter interval than that during which both of said first switches are operated simultaneously.

20. An implantable medical device comprising electrode means and means for sensing an electrical signal on said electrode means representative of physiological activity, characterized by said sensing means including means for generating a continuous sequence of bit samples, the two states of said bit samples representing changes in respective opposite directions in the sensed electrical signal, said bit sample generating means including capacitor means, means for charging said capacitor means, means for discharging said capacitor means, means for periodically comparing the potential across said capacitor means with the potential of the sensed electrical signal to derive bit samples the state of each of which represents the result of the most recent comparison, means for operating either said charging means or said discharging means in accordance with the state of each bit sample to control the potential across said capacitor means to track the potential of the sensed electrical signal, a constant current source, means for causing said constant current source to be utilized by both of said charging and discharging means to effect equal but opposite increments in the potential of said capacitor means independent of which of said charging or discharging means is operated in accordance with the state of each bit sample, means for holding said charging and discharging means unoperated during operation of said comparing means and for always holding said constant current source operated, and means for steering current from said constant current source away from said capacitor means whenever neither of said charging and discharging means is operated.

21. An implantable medical device comprising electrode means and means for sensing an electrical signal on said electrode means representative of physiological activity, characterized by said sensing means including means for generating a continuous sequence of bit samples, the two states of said bit samples representing changes in respective opposite directions in the sensed electrical signal, said bit sample generating means including capacitor means, means for charging said capacitor means, means for discharging said capacitor means, means for periodically comparing the potential across said capacitor means with the potential of the sensed electrical signal to derive bit samples the state of each of which represents the result of the most recent comparison, means for operating either said charging means or said discharging means in accordance with the state of each bit sample to control the potential across said capacitor means to track the potential of the sensed electrical signal, said capacitor means being connected in series between said electrode means and said comparing means, and each of said charging and discharging means including a set of switches connected to both sides of said capacitor means for delivering current to said capacitor means, the two sets of switches being connected so as to deliver currents to said capacitor means in respective opposite directions.

22. An implantable medical device in accordance with claim 21 wherein a first switch in one set is connected to one side of said capacitor means and a first switch in the other set is connected to the other side of said capacitor means, and further including means for applying a stimulating signal to said electrode means, and means for operating both of said switches simultaneously for a brief interval following the application of a stimulating signal to said electrode means to allow the potential across said capacitor means to rapidly recover to the potential ot the sensed electrical signal.

23. An implantable medical device in accordance with claim 21 further including means for shorting said electrode means briefly following the application of a stimulating current signal thereto to facilitate recovery of any charge stored in body tissues as a result of the stimulating signal, and means for causing said electrode means to be thus shorted for a shorter interval than that during which both of said first switches are operated simultaneously.

* * * * *